US009901329B1

(12) United States Patent
Polo

(10) Patent No.: US 9,901,329 B1
(45) Date of Patent: Feb. 27, 2018

(54) LAPAROSCOPIC MORCELLATING RECEPTACLE AND METHODS OF USE

(71) Applicant: Oscar Polo, Portland, OR (US)

(72) Inventor: Oscar Polo, Portland, OR (US)

( * ) Notice: Subject to any disclaimer, the term of this patent is extended or adjusted under 35 U.S.C. 154(b) by 0 days.

(21) Appl. No.: 15/382,119

(22) Filed: Dec. 16, 2016

(51) Int. Cl.
*A61B 17/00* (2006.01)
*A61B 17/32* (2006.01)
*A61B 17/34* (2006.01)
*A61B 17/3209* (2006.01)
*A61B 17/221* (2006.01)

(52) U.S. Cl.
CPC .. *A61B 17/00234* (2013.01); *A61B 17/32002* (2013.01); *A61B 17/3209* (2013.01); *A61B 17/34* (2013.01); *A61B 2017/00287* (2013.01); *A61B 2017/2212* (2013.01); *A61B 2017/320024* (2013.01); *A61B 2017/320064* (2013.01)

(58) Field of Classification Search
CPC ............ A61B 17/221; A61B 17/00234; A61B 17/32056
See application file for complete search history.

(56) References Cited

U.S. PATENT DOCUMENTS

| | | | | | |
|---|---|---|---|---|---|
| 5,176,687 A | * | 1/1993 | Hasson | ............ | A61B 17/00234 606/114 |
| 5,215,521 A | * | 6/1993 | Cochran | .......... | A61B 17/00234 128/898 |
| 5,352,184 A | * | 10/1994 | Goldberg | ................ | A61B 10/04 128/DIG. 24 |
| 5,465,731 A | * | 11/1995 | Bell | .................. | A61B 17/00234 600/37 |
| 5,618,296 A | * | 4/1997 | Sorensen | .......... | A61B 17/32002 606/167 |
| 5,735,289 A | * | 4/1998 | Pfeffer | ............. | A61B 17/00234 600/562 |
| 5,785,677 A | * | 7/1998 | Auweiler | ......... | A61B 17/00234 128/850 |
| 5,788,709 A | * | 8/1998 | Riek | ................ | A61B 17/00234 606/110 |
| 6,228,095 B1 | * | 5/2001 | Dennis | ............. | A61B 17/00234 606/114 |
| 2006/0058776 A1 | * | 3/2006 | Bilsbury | .......... | A61B 17/00234 604/540 |
| 2007/0073251 A1 | * | 3/2007 | Zhou | ...................... | A61B 10/00 604/327 |
| 2009/0043315 A1 | * | 2/2009 | Moon | .............. | A61B 17/00234 606/114 |
| 2011/0190781 A1 | * | 8/2011 | Collier | ............. | A61B 17/00234 606/114 |
| 2012/0083795 A1 | * | 4/2012 | Fleming | ........... | A61B 17/00234 606/114 |

(Continued)

*Primary Examiner* — Christopher L Templeton
(74) *Attorney, Agent, or Firm* — Baumgartner Patent Law

(57) ABSTRACT

A collapsible and expandable receptacle that can be inserted into a patient's cavity through a laparoscopic port (sleeve) is disclosed herein. The receptacle is configured so that when it enters the cavity it can be expanded or opened into a shape of a bowl or cone. A targeted tissue specimen can then be placed inside the expanded receptacle, and the surgeon has the room and visibility to cut the tissue with a power morcellator and avoid severing the bag or spreading unwanted particulate tissue to other areas inside the patient. Once the specimen has been cut and removed, the empty receptacle can be collapsed and removed out the same tissue removing sleeve.

22 Claims, 14 Drawing Sheets

(56) References Cited

U.S. PATENT DOCUMENTS

| | | | |
|---|---|---|---|
| 2012/0109144 A1* | 5/2012 | Chin | A61B 17/00 606/114 |
| 2012/0158010 A1* | 6/2012 | Menn | A61B 17/00234 606/114 |
| 2012/0232423 A1* | 9/2012 | Menn | A61B 17/00234 600/562 |
| 2012/0277758 A1* | 11/2012 | Davis | A61B 17/00234 606/114 |
| 2013/0325025 A1* | 12/2013 | Hathaway | A61B 17/00234 606/114 |
| 2014/0236168 A1* | 8/2014 | Shibley | A61M 13/003 606/114 |
| 2015/0320409 A1* | 11/2015 | Lehmann | A61B 17/221 600/109 |
| 2016/0100857 A1* | 4/2016 | Wachli | A61B 17/3439 600/204 |
| 2016/0262763 A1* | 9/2016 | Shankarsetty | A61B 17/1285 |
| 2016/0338682 A1* | 11/2016 | Hoyte | A61B 17/00234 |
| 2017/0245839 A1* | 8/2017 | Malkowski | A61B 10/02 |

* cited by examiner

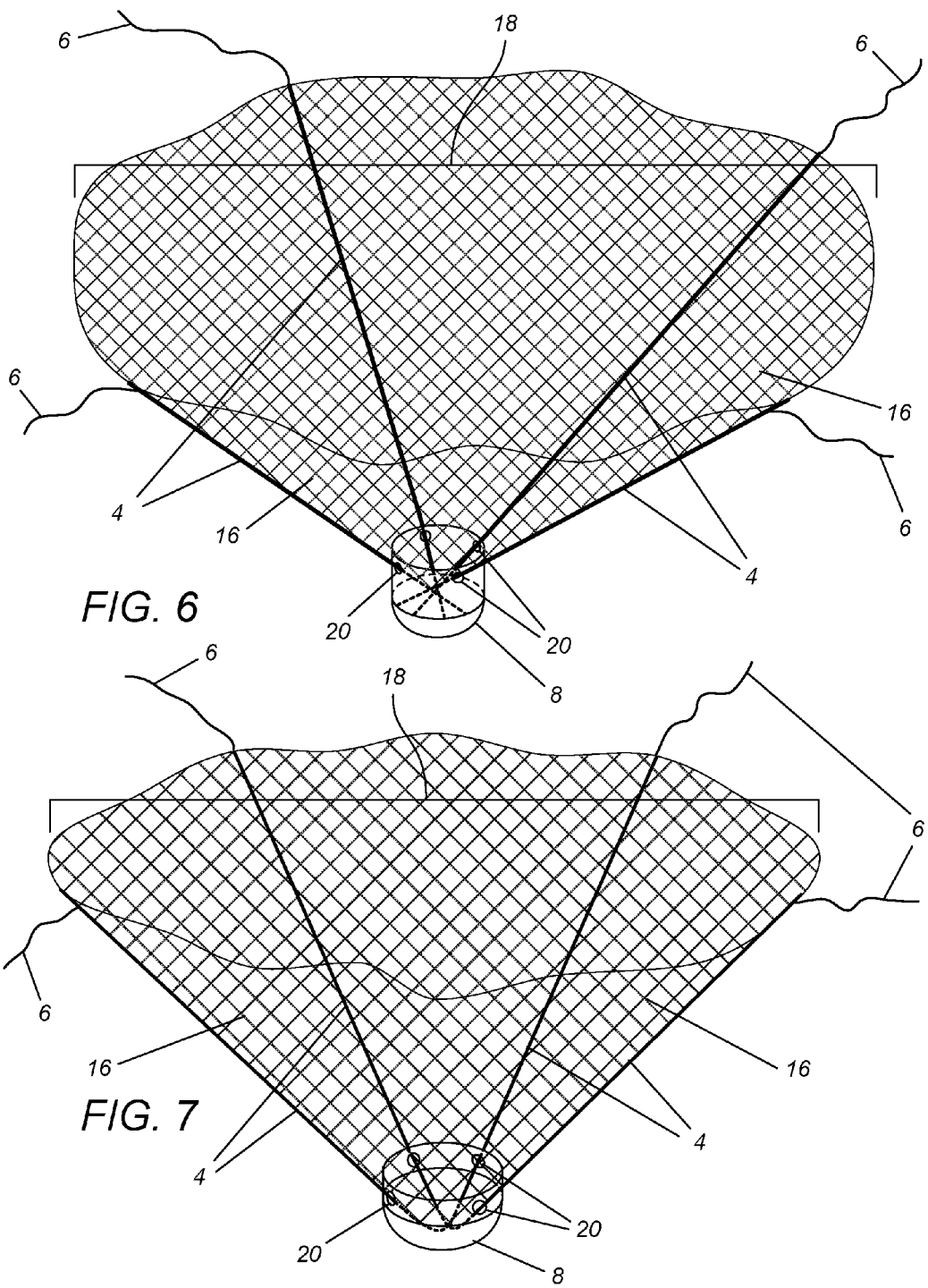

LAPAROSCOPIC MORCELLATING RECEPTACLE AND METHODS OF USE

FIELD OF THE INVENTION

The teachings herein relate to methods and compositions useful in laparoscopic power morcellation. More specifically, the embodiments herein relate to receptacles configured to prevent morcellated particulate tissue, from spreading into nearby areas from the cutting site.

BACKGROUND

Power morcellators are devices, used in laparoscopic surgery that morcellate, or cut tissue, into smaller pieces to allow for removal through small surgical access sites. Currently laparoscopic power morcellation for the removal of the uterus (hysterectomy) or uterine fibroids (myomectomy) in women is discouraged because, based on an analysis of currently available data, it may pose a risk of inadvertently spreading cancerous tissue, notably uterine sarcomas, beyond the uterus.

In trying to prevent the potential spread of cancerous tissue, morcellation receptacles have been designed to contain the specimen that is being cut and to remove the severed pieces as they are being cut. Current receptacles for laparoscopic surgery are used for retrieving specimen. They have an expandable and collapsing collar at the opening that is attached to a hanging bag that opens enough to accommodate the targeted tissue. Unfortunately, these current receptacles do not give the surgeon the room or visibility to perform power morcellation within them without the risk of severing the receptacle. Other receptacles are designed for morcellation with a hand held scalpel as opposed to power morcellation. These receptacles have the opening of the bag external to the cavity so that the tissue inside the receptacle can be visibly severed and removed through the expanded incision on the abdominal wall. An inflatable bag design was recently approved for use with both a handheld scalpel or power morcellator, but this bag's small opening significantly limits the use of a power morcellator and laparoscope because there is not sufficient room for the surgical cutting device to move and cut within the bag. Furthermore, this bag is inflatable and so severing or puncturing this bag would make it ineffective for its intended use. Preferred receptacles herein are not inflatable.

Accordingly there is a need in the art for receptacles configured to give the medical practitioner (e.g., surgeon) enough room and visibility to perform power morcellation, within them, using the spaced apart laparoscopic ports already in place for the intended surgical procedure, and that allows for improved handling and visibility of the specimen and decreases the likelihood of severing the receptacle. The following disclosure describes expanding/collapsing receptacles configured for use with power morcellators that address this need in the art.

SUMMARY

Preferred embodiments are directed to morcellation receptacle systems comprising a collapsible receptacle, having a vertical axis with a lower half section with a distal end and an upper half section with a proximal end, and a horizontal axis, configured such that when collapsed on its horizontal axis, it is linearly sized to fit within and through an opening between 14-20 mm in width but not when expanded in a natural open position; said receptacle comprising: a distal area; a plurality of at least three support rods positioned in a circumferential and equidistant manner around the vertical axis, or substantially so, and having proximal ends extend proximally and laterally away from the distal area and configured such that the support rods can move towards each other on the horizontal axis when the receptacle is collapsing and move away from each other on the horizontal axis when the receptacle is opening, a flexible liner that is water resistant, low-friction, tear-resistant, and made of material different from the support rods, having a thickness between 0.05-0.15 mm, wrapped along the support rods such as to define a bag with a closed end at the distal base and a proximal opening in the upper half of the receptacle having a width between 14-30 cms; and a plurality of at least three support filaments having distal ends coupled to the upper half section of the receptacle in a circumferential manner and configured such that when proximal ends of the support filaments are pulled away from each other, the receptacle is moved in a proximal direction and is maintained in an open position.

Preferred methods of morcellating a targeted piece of tissue in a subject comprise: a) providing the morcellation receptacle system of claim 1; b) creating one or more incisions in the subject near the targeted piece of tissue, wherein the incision has a width of between 14-20 mm and inserting a first trocar sleeve into a first incision; c) collapsing the receptacle; d) inserting the collapsed receptacle inside of the subject through the first trocar sleeve; e) opening the proximal opening of the receptacle; f) positioning the targeted tissue into the receptacle such that cut pieces of the targeted tissue will remain within the receptacle; g) positioning a morcellator into the proximal opening of the receptacle and cutting the target tissue; h) removing the cut targeted tissue from the receptacle through the first trocar sleeve; and i) collapsing the receptacle and withdrawing it from inside the subject through the first trocar sleeve.

BRIEF DESCRIPTION OF THE DRAWINGS

It will be appreciated that the drawings are not necessarily to scale, with emphasis instead being placed on illustrating the various aspects and features embodiments of the invention, in which:

FIG. 6 is a perspective view of an opened receptacle of FIG. 5.

FIG. 7 is a perspective view of an opened receptacle having 2 rods that bend through the distal base.

DETAILED DESCRIPTION OF THE ILLUSTRATED EMBODIMENTS

Embodiments of the present invention are described below. It is, however, expressly noted that the present invention is not limited to these embodiments, but rather the intention is that modifications that are apparent to the person skilled in the art and equivalents thereof are also included.

Figure 1:
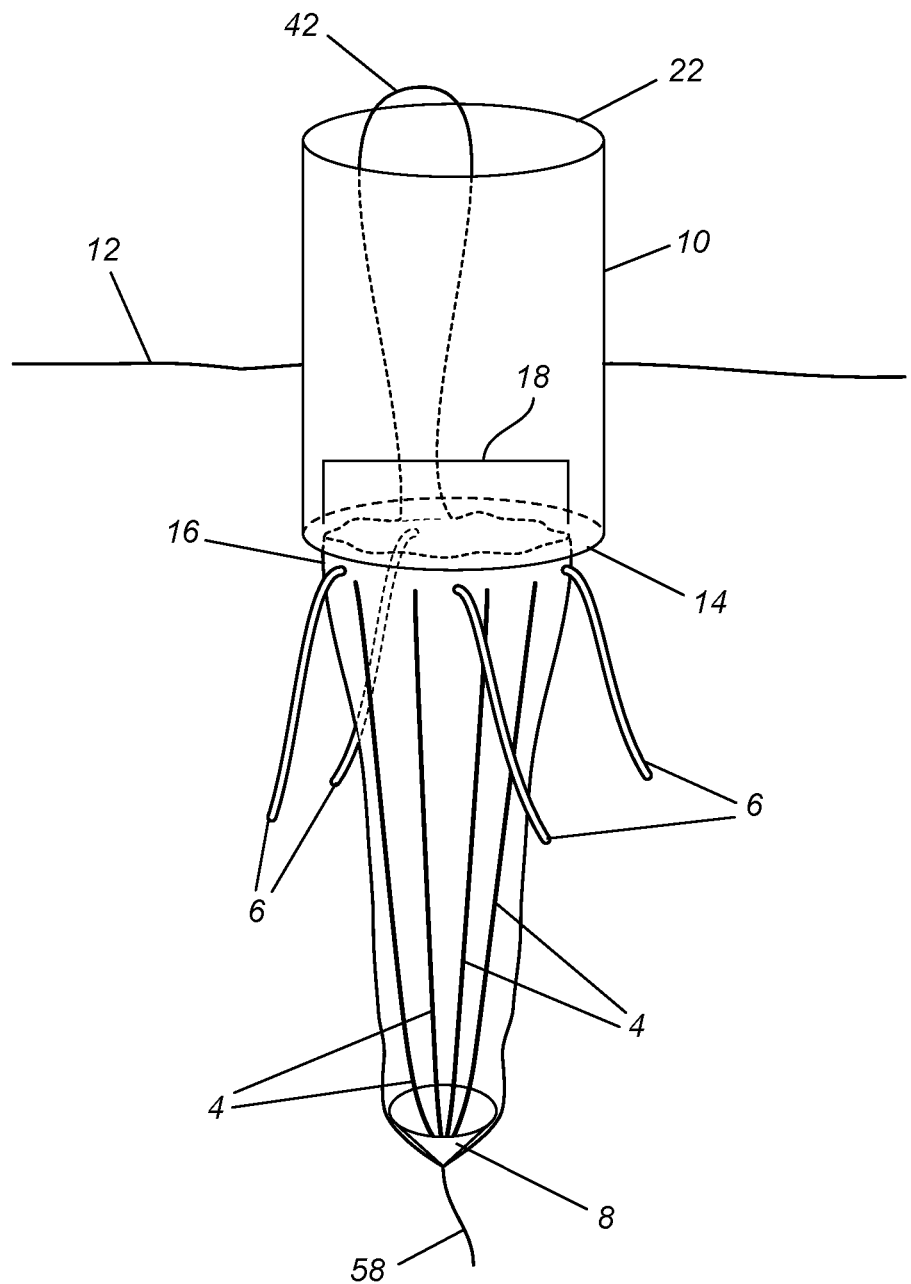
FIG. 1 is a perspective view of a collapsed receptacle passing through a trocar sleeve penetrating a patient's abdominal wall.
Figure 2:
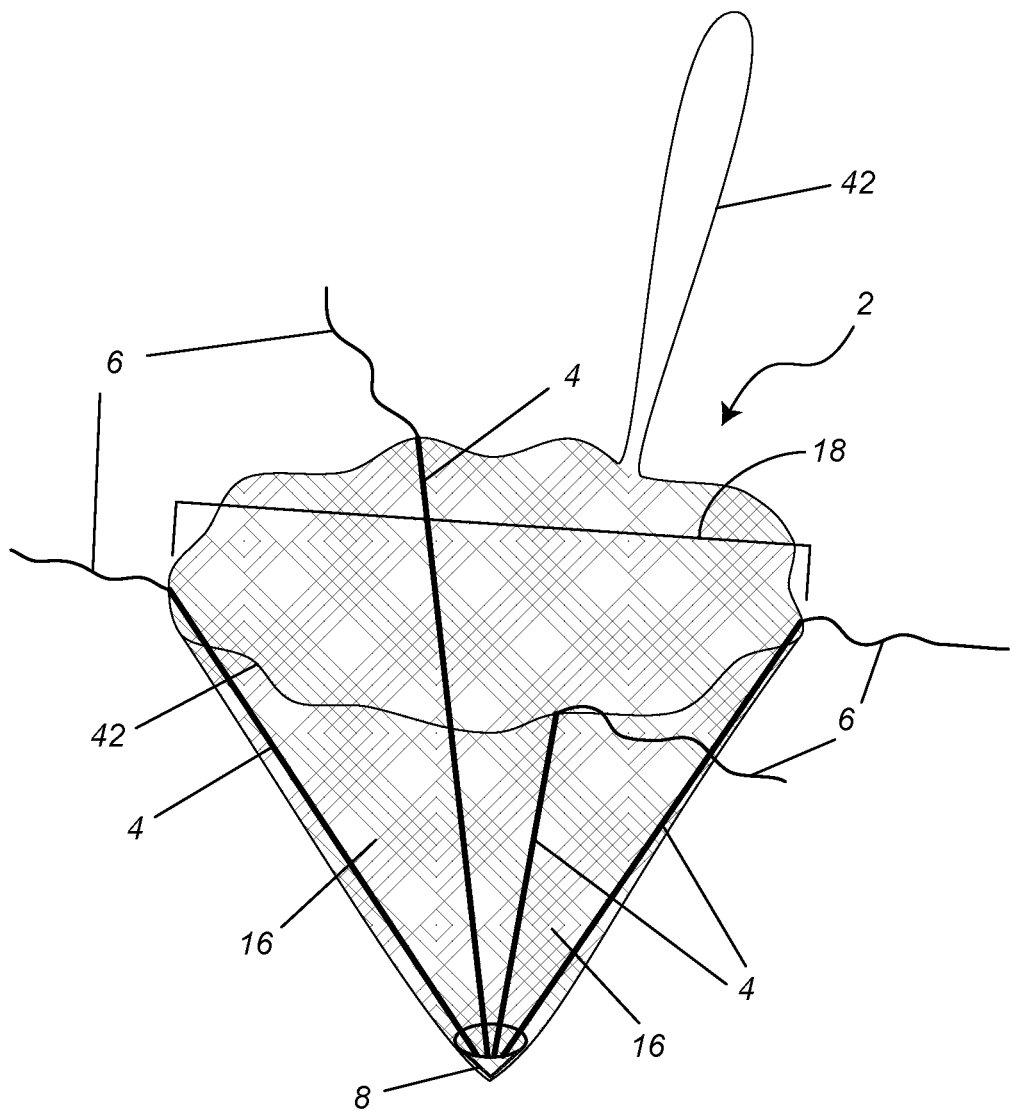
FIG. 2 is a perspective view of an opened receptacle having straight support rods coupled to filaments.

FIGS. 1 and 2 show the receptacle 2 in a collapsed/closed position and an open position respectively. The collapsed configuration shown in FIG. 1 and the open configuration of FIG. 2 both depict the receptacle 2, having a plurality of support rods 4 coupled to a distal base 8. The receptacle 2 has a vertical axis with a lower half section and a distal end, and an upper half section with a proximal opening 18.

Figure 3:
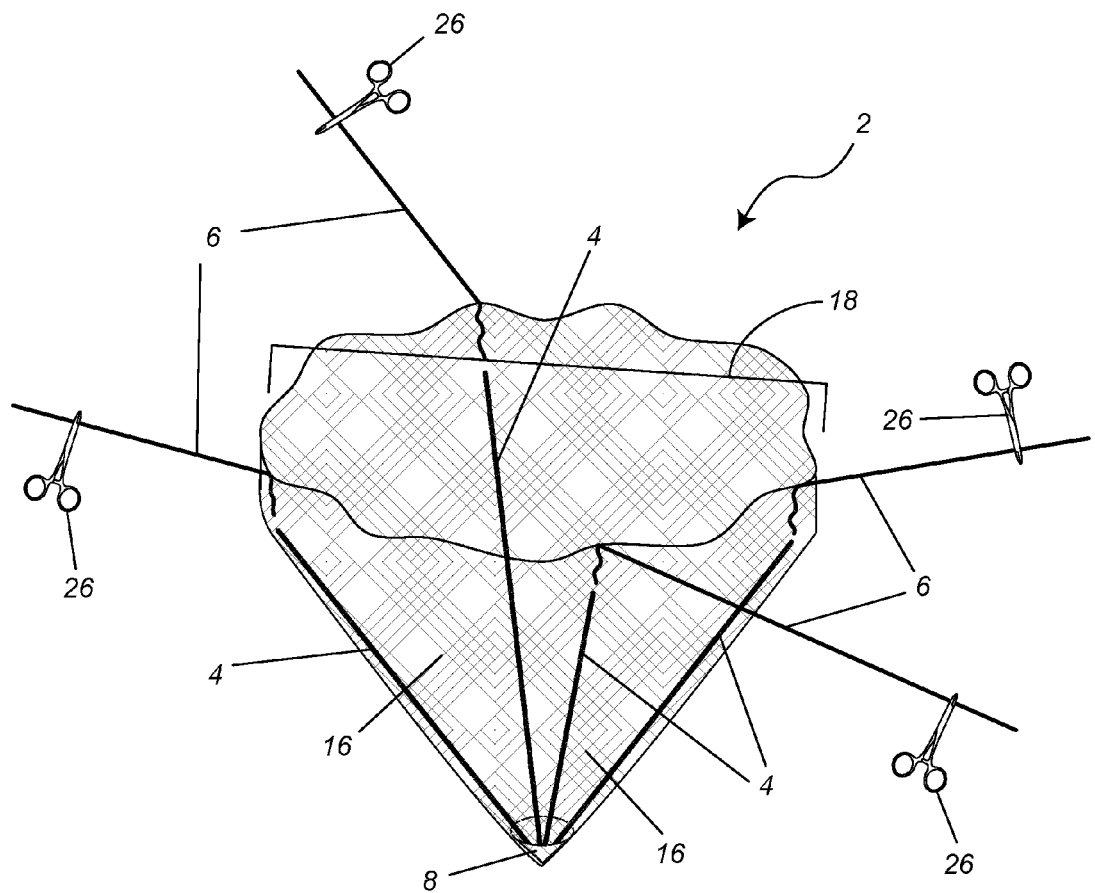
FIG. 3 is a perspective view of an opened receptacle having straight support rods not coupled to filaments.

In FIG. 1, the closed receptacle 2 is shown passing through the inside of a trocar sleeve 10, which can non-exclusively include any suitable laparoscopic port or sleeve used in surgery. The receptacle has a liner 16, made of a thin, flexible material that is fluid impermeable, and preferably is hypoallergenic, has a low coefficient friction, and is made of a tear-resistant material such as ripstop nylon, polyurethane, or polyisoprene. Latex could be a suitable material as well, such as for situations where neither the patient nor medical practitioner is allergic. The flexible liner 16 is wrapped along the support rods 4 (it can be on the outside and/or inside of the rods 4) such as to define an enclosed space, or bag, with a proximal opening 18 defined by proximal/upper portion of the flexible liner 16. According to preferred embodiments, such as when the rods 4 are flexible, they can maintain the shape of the open receptacle 2, such as a bowl shaped, for example. According to further embodiments, the rods are coupled to the bag in a direction which keeps the rods from sliding right or left. In FIG. 1, the proximal ends of the support rods 4 traverse up from the distal base 8 to the proximal opening 18. This is merely optional, however. As an alternative, the support rods 4 only traverse up to the upper proximal section of the flexible liner 16, such as shown in FIG. 3. Advantageously the flexible liner 16 creates a waterproof seal, water resistant, or impermeable barrier to blood or particular tissue around the working space, with the exception of the proximal opening 18. Thus, according to preferred embodiments, the proximal opening 18 is the only opening, or access point, of the receptacle 2.

The trocar sleeve 10 is positioned through a patient's outer body, or more specifically their abdominal wall 12 such that its proximal opening 22 is located outside of the patient which leads through the hollow trocar sleeve 10 to a distal opening 14 within the patient's body, or more specifically their abdominal cavity. According to preferred embodiments, in the collapsed configuration, the receptacle 2 has a small enough width or diameter to fit within the trocar sleeve 10 and pass through the proximal and distal openings 22 and 14. Preferred embodiments of receptacles 2 can fit through a trocar sleeve 10 having a hollow internal channel with a diameter or width of about 15 mm, such as 10-20 mm. These dimensions are also applicable for the proximal and distal openings 22 and 14 of the trocar sleeve 10. This configuration can be accomplished using any suitable dimensions, for example, by measuring or approximating the width of the collapsed rods 4, so that at maximal measurement or approximation of the diameter of collapsed rods 4 is less than the diameter/width of the hollow channel within the trocar sleeve 10. Suitable diameters/widths of the collapsed rod can thus be about 14 or 14.5 mm including between 9-19 mm. Similarly, the distal base 8 should be sized to likewise fit though the hollow channel within the trocar 10 and its proximal and distal openings 22 and 14. Thus, in general, the distal base's width/diameter should be less than the diameter/width of the hollow channel within the trocar sleeve 10, including the proximal and distal openings 22 and 14. These widths/diameters can be about 14 or 14.5 mm including between 9-19 mm. Embodiments herein further contemplate instances where the rods 4 and/or distal base 8 are made of flexible or elastic material, and their widths/diameters in a closed configuration could be the same or larger than the width/diameter of the hollow channel within the trocar sleeve 10, including the proximal and distal openings 22 and 14, so long as the rods 4 and distal base 8 can further compress/collapse to pass through the trocar sleeve. As a non-exclusive example, the support rods 4 and/or the distal base 8 can be made of an elastic material such as nitinol, also known as nickel titanium.

Figure 10:
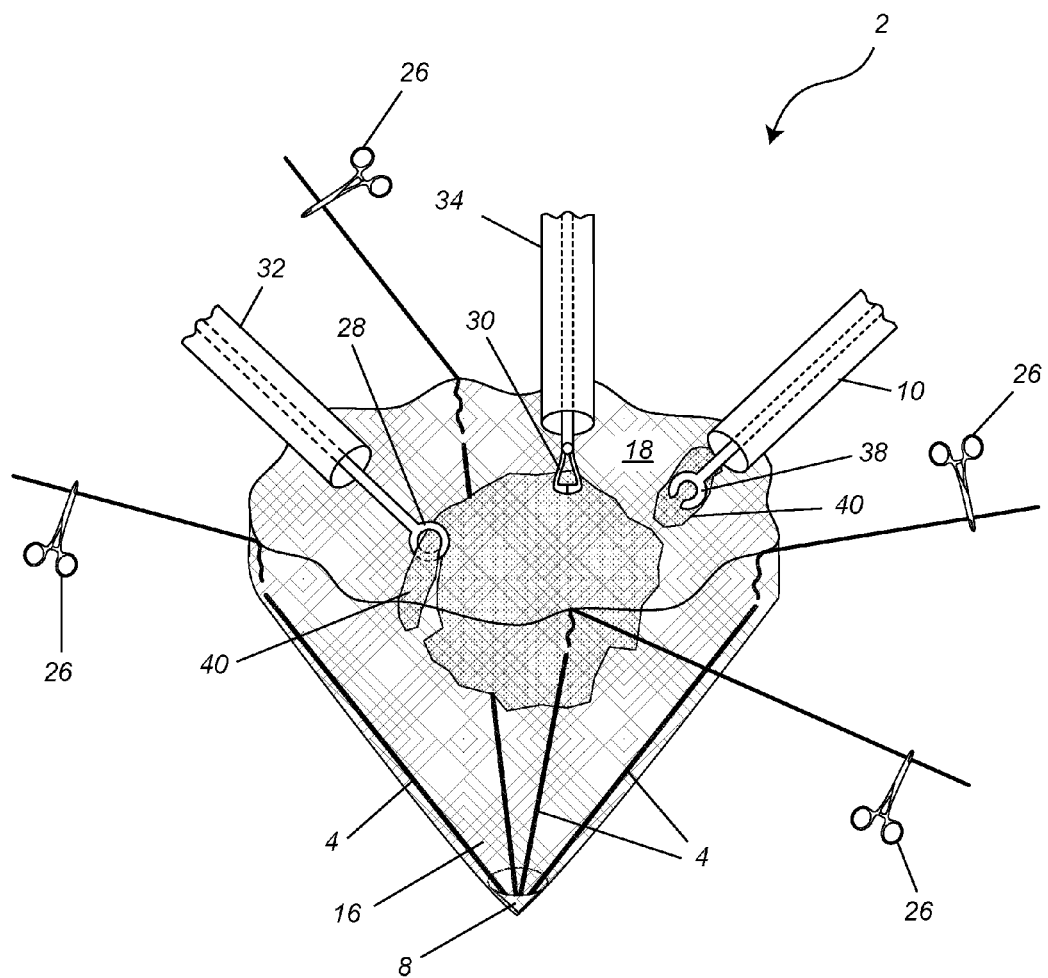
FIG. 10 is a perspective view of a tissue sample being morcellated and removed within an opened receptacle.
Figure 11:
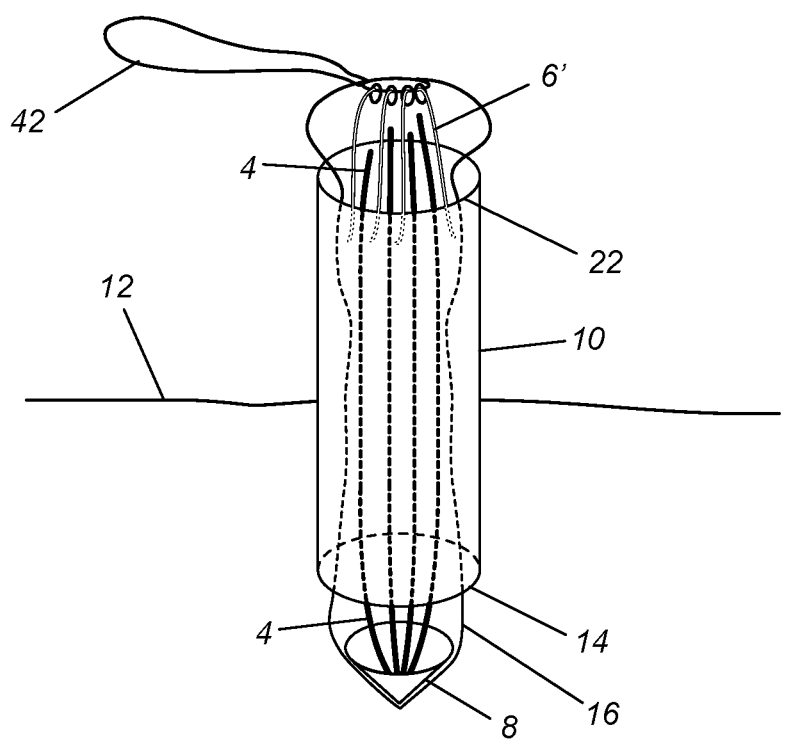
FIG. 11 is a perspective view of a collapsed receptacle having a draw string and positioned within a laparoscopic sleeve penetrating a patient's abdominal wall.

As shown in FIG. 2, the receptacle 2, in its open position, is shaped as a cone or bowl, for containment of the specimen, trocar sleeves, and surgical instruments, such as graspers, laparoscopes, and the morcellator. While non-limiting, it is preferred that the receptacle 2 is in a bowl shape rather than a funnel shape to accommodate the specimen 40 better. The receptacle 2 can also be cone shaped or concave as well. A main objective of the present embodiments is to provide a receptacle 2 that is small enough to travel through a trocar sleeve 10 (whether through insertion or extraction), yet also expand large enough to surround a working space which can include a target specimen 40 and multiple trocar sleeves and instruments for cutting, grasping, viewing, and extracting the specimen from the patient. FIG. 10 is an exemplary figure showing various instruments 28, 30, 38 grasping and cutting a specimen 40 that the receptacles 2 herein are configured to surround when positioned inside a patient. Accordingly, preferred proximal opening 18 diameters are between 14-30 cm, when the receptacle 2 is in an open position, such as shown in FIGS. 2 and 10. The proximal opening 18 can be of any suitable shape to accommodate the specimen 40 and desired instruments, such as circular or oval, for example. The proximal half of the cone shaped bag can include a collar of 2-5 cm in length that is made of the same fabric that is continuous with the vertical axis of the bag and maintains the shape throughout its length. In FIG.

4B, the area of liner 16 between the proximal ends of the rods 4 and the proximal opening 16 can be considered the collar.

Figure 4A:
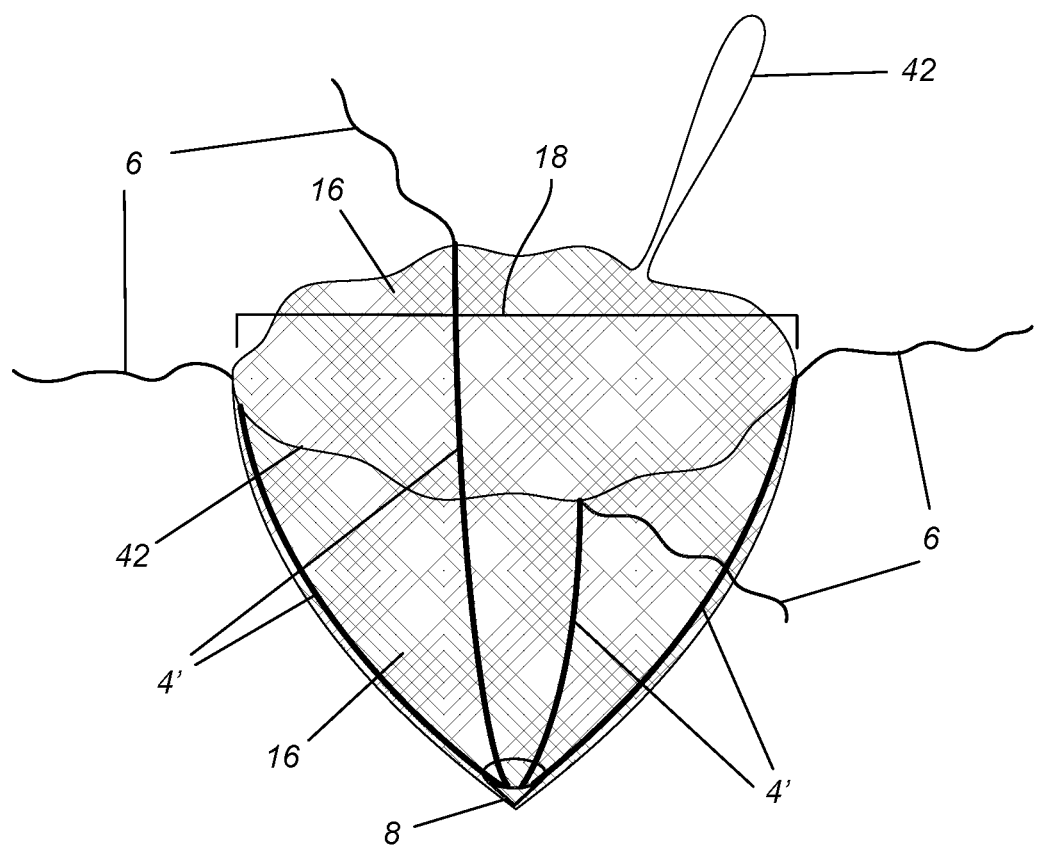
FIG. 4A is a perspective view of an opened receptacle having a drawstring and concave support rods coupled to filaments.
Figure 4B:
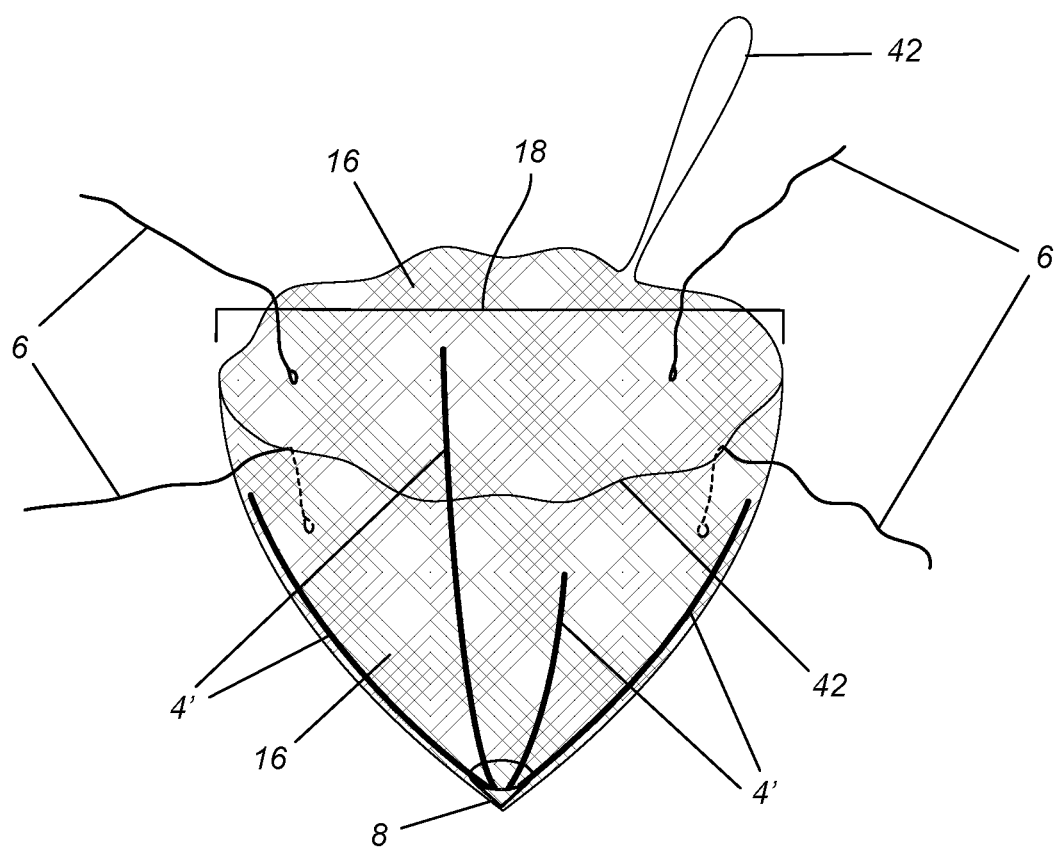
FIG. 4B is a perspective view of an opened receptacle having a drawstring and concave support rods not coupled to filaments.

In FIG. 2, the receptacle 2 has a distal base 8 that is operably coupled to a plurality of support rods 4 which extend to proximal ends that define a proximal opening 18 of the receptacle 2. In other embodiments, the support rods 4 and 4' do not extend to the proximal opening 18, such as shown in FIGS. 3 and 4B. In FIGS. 3 and 4B, the support rods 4 and 4' extend proximally to the upper half of the receptacle 2, but not to the perimeter of the proximal opening 18. While discussion herein is primarily directed to support rods 4, those with skill in the art will appreciate that disclosure herein pertaining to these features are readily interchangeable to other shapes of support rods, such as support rods 4', where suitable. The distal base is also couple to the distal end of the liner.

The proximal ends of the support rods 4 and are configured to move towards each other when the receptacle 2 is collapsing and move away from each other when the receptacle 2 is opening. According to preferred embodiments, the receptacle 2 has a frame of (3-8) of axial support rods 4 that are circumferentially, attached to the distal base 8, preferably at equidistant lengths from each other. These numbers are non-limiting, but preferably four rods 4 are used. The support rods 4 can be shaped in any suitable manner, non-exclusively including straight rods, or curvilinear, such as concave and convex rods, and other suitable shapes, when in the expanded position. FIG. 2 shows an open receptacle 2 having straight support rods 4 that distally converge from their proximal ends to the distal base 8. FIGS. 4A and 4B show an open receptacle 2 having concave support rods 4' that distally converge from their proximal ends to the distal base 8. Additionally, the support rods 4 can non-exclusively be: rigid, adjustable, hinged, jointed, telescoping, flexible, or elastic. Preferably the rods 4 have a natural spring tension that allows them to expand outward when not confined within the trocar sleeve 10 and to collapse inward when traveling through the hollow channel of the trocar sleeve 10.

Figure 4C:
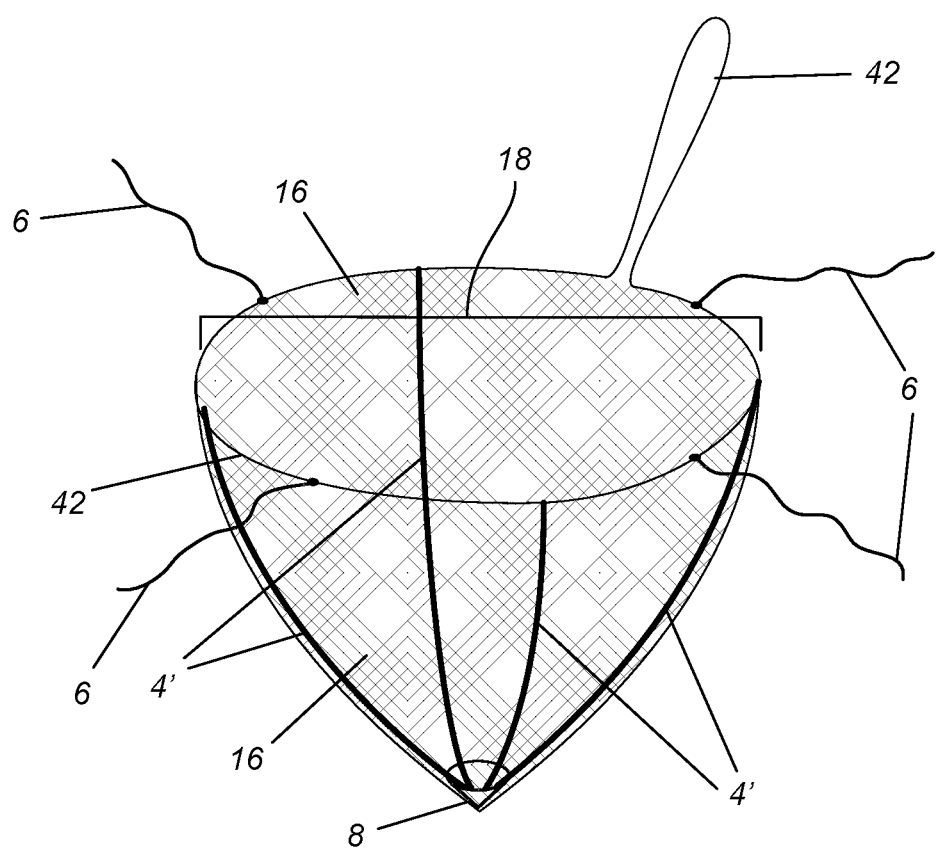
FIG. 4C shows a perspective view of an opened receptacle having a nitinol wire as a drawstring.

FIGS. 1 and 2 also show a drawstring 42 that circumnavigates around the vertical axis of the proximal opening 18 of the receptacle and configured such that when the drawstring 42 is tightened, the opening of the receptacle narrows; the proximal ends of the support rods move toward each other, thereby collapsing the receptacle on its horizontal axis. The drawstring 42 can be coupled to the flexible liner 16 using any suitable way, such as threading the drawstring 42 through loops or a channel within the liner 16 or weaved/threaded through the liner 16 itself. The drawstring 42 can be tightened using any suitable method, such as pulling it in a proximal direction whether manually or with an instrument. Conversely, when the drawstring 42 is loosened, the proximal ends of the support rods move away from each other, thereby expanding the bag to its open position, such as shown in FIG. 2. The drawstring 42 can be made of any suitable material that has elasticity and will aid in expansion of the proximal end and help maintain the liner 16 on the proximal end from folding on itself when in the open position such as nylon, or thin nitinol, such as 0.25 mm caliber nitinol. FIG. 4C shows a drawstring 42 that is made of nitinol and wherein the filaments 6 are not attached to the rods 4' but the perimeter of the proximal opening 18.

The receptacles herein have a plurality of at least three, or four, support filaments 6 having distal ends coupled to the upper half section of the receptacle in a circumferential manner and configured such that when proximal ends of the support filaments are pulled away from each other, the receptacle 2 is moved in a proximal direction and is maintained in an open position. According to preferred embodiments, the proximal ends/sections of the filaments 6 are brought out of the anterior abdominal wall and can be anchored using any suitable device such as pins or clamps 26 to stabilize the receptacle 2 and maintain it in its open position, such as shown in FIG. 10. The filaments 6 can be spaced apart equidistant around the receptacle 2, (e.g., 90 degrees apart from each other) see FIG. 14 square configuration, or otherwise sufficiently apart from each other, such as at least 45 degrees from each other around the circumference of the receptacle 2. The filaments 6 can be a string or made of any suitable material with elasticity that are configured to stand erect in their natural position for easier grasping by the surgeon. Preferred filaments 6 are connected to the proximal end 18 of the receptacle 2 and not weaved through the collar, to prevent the receptacle 2 from folding in on itself. Preferred filaments 6 are made of thin nitinol, including 0.25 mm caliber nitinol.

According to certain embodiments, the proximal sections of the rods 4 can be coupled to filaments 6 (see FIGS. 2 and 4A) such that when pulled close inwardly, the rods 4 collapse so that the receptacle 2 can pass through the trocar 10 whether being inserted or extracted. Likewise, by pulling the proximal end of the rods 4, such as through pulling the filaments 6 outwardly, the proximal sections of the rods 4 diverge during opening. The filaments 6 can be coupled to any part of the upper half section of the receptacle 2, including the proximal sections of the rods 4, the flexible liner 16, or the rim around the proximal opening 18 of the receptacle, using any suitable way, including adhesives, tying, heat, etc.

Figure 14:
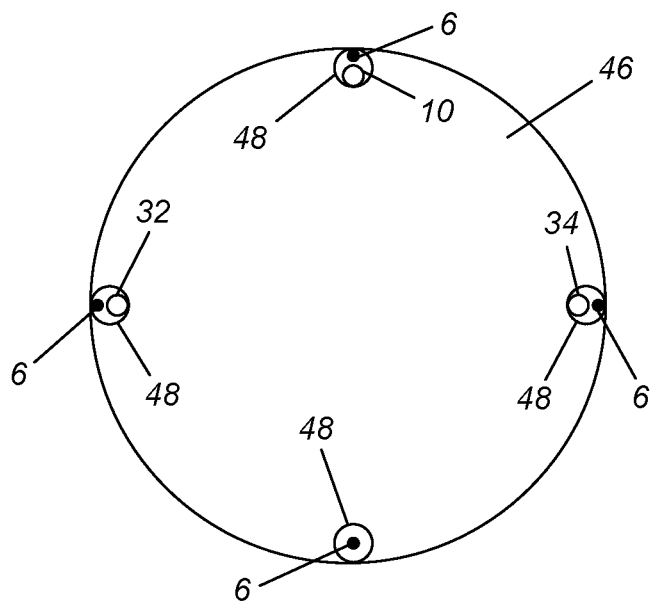
FIG. 14 shows a top view of a lid with four holes spaced equidistantly along the perimeter of the lid (e.g., 90 degrees apart), in a square or diamond configuration.
Figure 15:
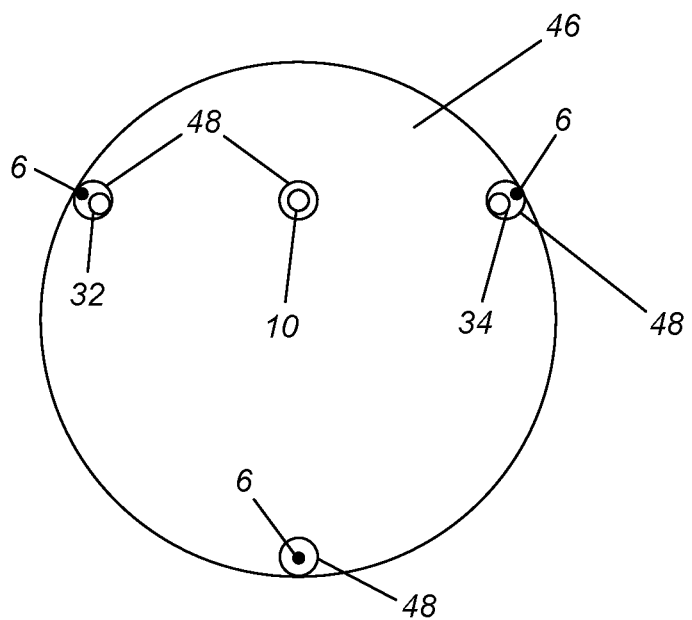
FIG. 15 shows a top view of a lid with four holes spaced apart. The three filaments and their respective holes form a triangle, that is preferably equilateral such that the filaments are equidistant apart from each other with respect to the triangular formation as opposed to their position on the perimeter of the lid.

For purposes of this description there are preferably two to four filaments 6, but more support filaments can be attached and anchored anteriorly, to stabilize the receptacle 2 during morcellation. Even more preferably, the embodiments herein use 3 or 4 filaments 6 spaced apart from each other equidistantly. Additionally, FIG. 14 shows four filaments 6 spaced every 90 degrees around a circular lid 46. FIG. 15 shows three filaments that aren't arranged equidistantly apart from each other around the perimeter of the lid 46, but form a triangle, which could be an equilateral triangle. For both FIGS. 14 and 15 the trocar 10 is preferably inserted through the navel of the patient.

Figure 5:
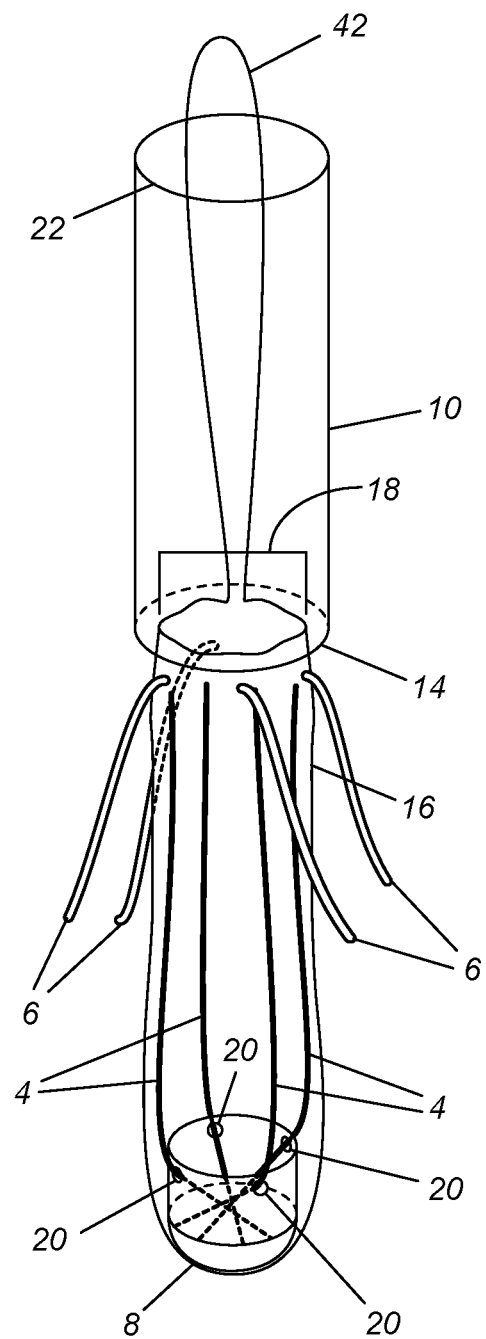
FIG. 5 is a perspective view of an alternative collapsed receptacle passing through a trocar sleeve and having rods that couple to the distal base.
Figure 8:
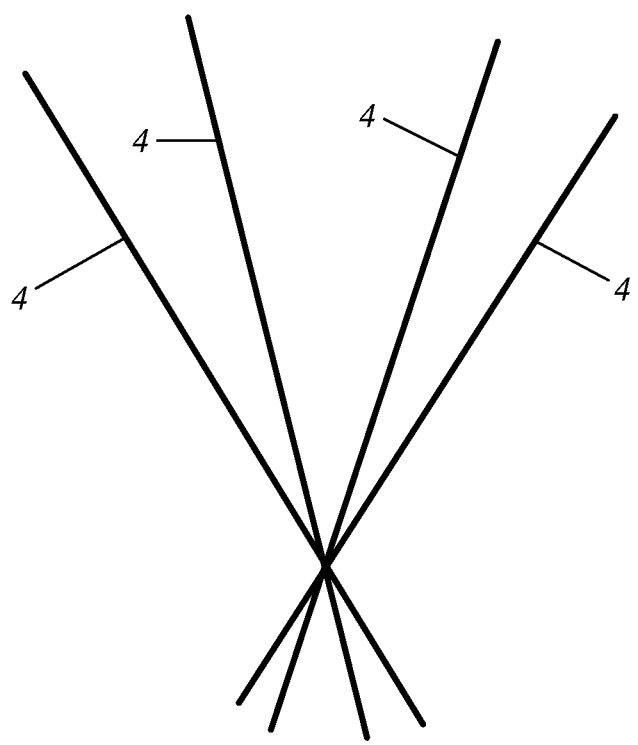
FIG. 8 is a perspective view of the rods in the receptacle shown in FIGS. 5 and 6.
Figure 9:
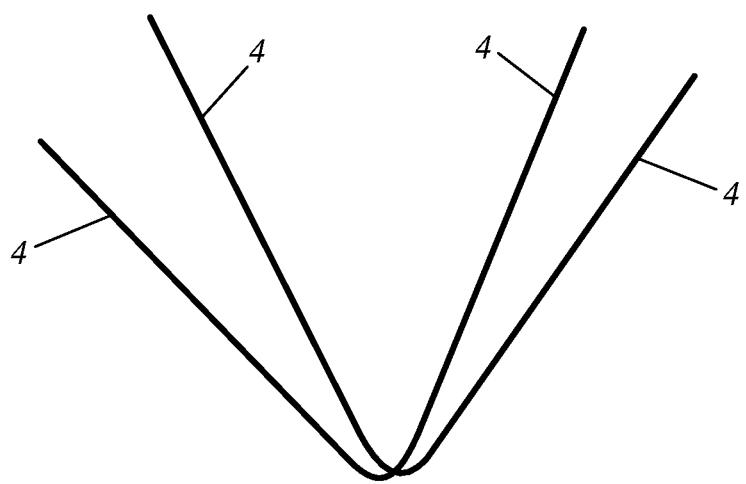
FIG. 9 is a perspective view of elastic rods that bend through the distal base of the receptacle shown in FIG. 7.

The distal sections of the rods 4 can be coupled to the distal base 8. While the rods 4 described herein can couple to the distal base 8 in any suitable way, FIGS. 5 and 6 depicts a half-capsule shape (half of a spherocylinder) distal base 8 having apertures 20 configured for receiving the distal sections of the rods 4. FIG. 8 is a close-up view of the distal sections of the four rods 4 that couple to the distal base 8 shown in FIGS. 5 and 6. In contrast, FIG. 7 also depicts a half-capsule shape (half of a spherocylinder) distal base 8 having apertures 20 configured for receiving the distal sections of the rods 4. According to this embodiment, the rods 4 curve through the distal base 8, thereby providing natural spring tension when the rods 4 are compressed within the trocar 10 so they can spring open upon passing through the trocar's distal opening 14. FIG. 9 is a close-up view of the distal sections of elastic rods 4 that do not connect to the distal base 8, but rather form a U or V-shape.

Figure 12:
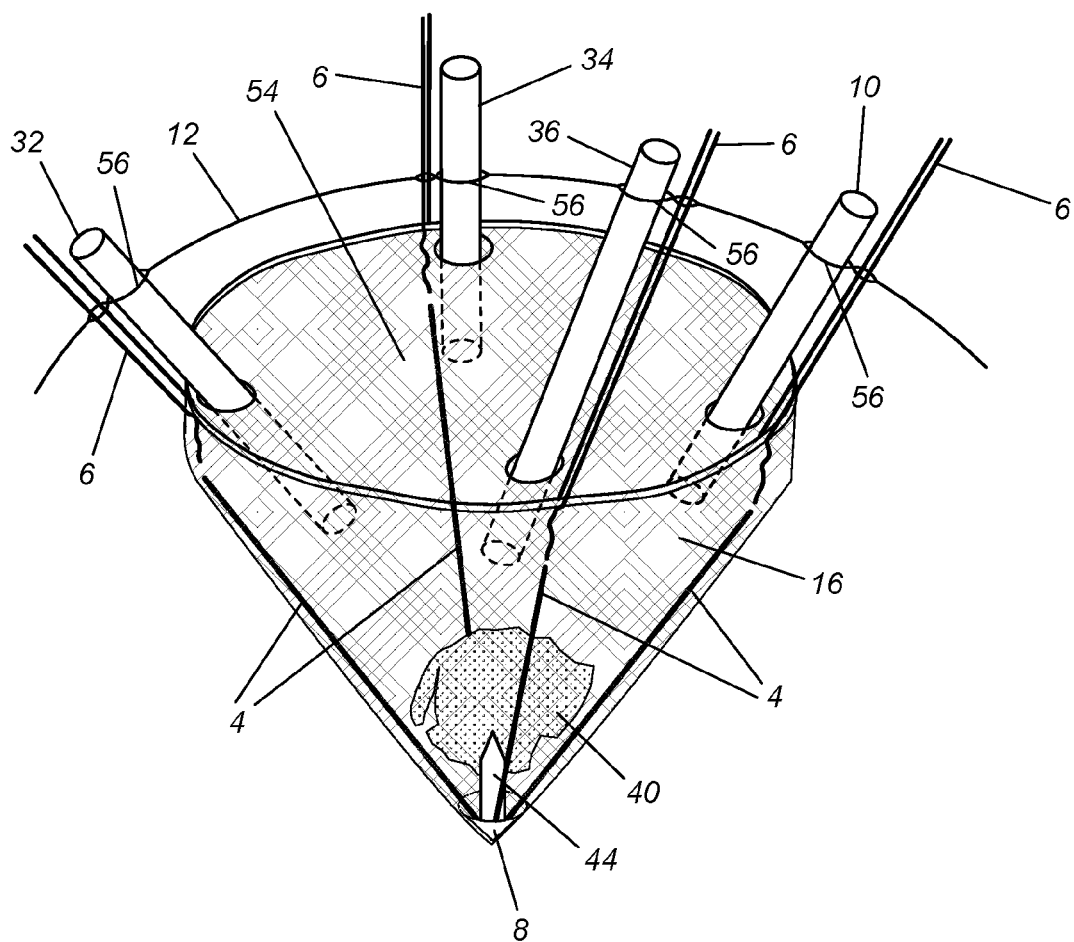
FIG. 12 is a perspective view of an open receptacle having a membrane cover penetrated by four laparoscopic sleeves.

FIG. 10 shows a targeted tissue specimen 40 and multiple instruments grasping and cutting it within an open receptacle 2. The tissue grasper 38 can serve two purposes: one to help stabilize the tissue 40 as it is being cut and the other is to pull the cut pieces out of the patient, such as through the main trocar sleeve 10, which can be any suitable size, but is preferably 15 mm, or 10-20 mm. The power morcellator 28 is shown cutting the tissue specimen 40 and is positioned through a trocar sleeve 32 that is preferably about 8 mm (e.g., 5-8 mm) in diameter, but can be any suitable size. A second tissue grasper 30 traversing through its trocar sleeve 34 is shown that can optionally help stabilize the tissue specimen 40 during morcellation. This trocar sleeve 34 is preferably about 8 mm in diameter, but can be any suitable size. Additional instruments can likewise be utilized within the open receptacle 2, such as a laparoscope. FIG. 12 shows a fourth trocar sleeve 36 that a laparoscope or other instrument can be traversed though. The fourth trocar sleeve 36 can be any suitable diameter such as 5 mm, for example.

In FIG. 12, the proximal opening 18 of the receptacle 2 is covered by a membrane lid 54, that is collapsible when the receptacle 2 is in a closed position, and can expand, or flatten out, when the receptacle 2 opens. The membrane 54 is thin enough that trocar sleeves 10, 32, 34, and 36 can be pressed down manually and puncture the membrane at holes 56, such that the instruments 28, 30, and 38 can be positioned into the open receptacle 2. Any suitable number of trocar sleeves can puncture the membrane 54 depending on the circumstances. For example, 2-6 trocar sleeves could be used to puncture the membrane 54. FIG. 12 also shows a spike 44 that extends proximaly from and is operably coupled to the distal base 8. According to these embodiments, the user can pierce the tissue specimen 40 onto the spike 44 thereby helping to stabilize the tissue 40 during cutting.

Figure 13:
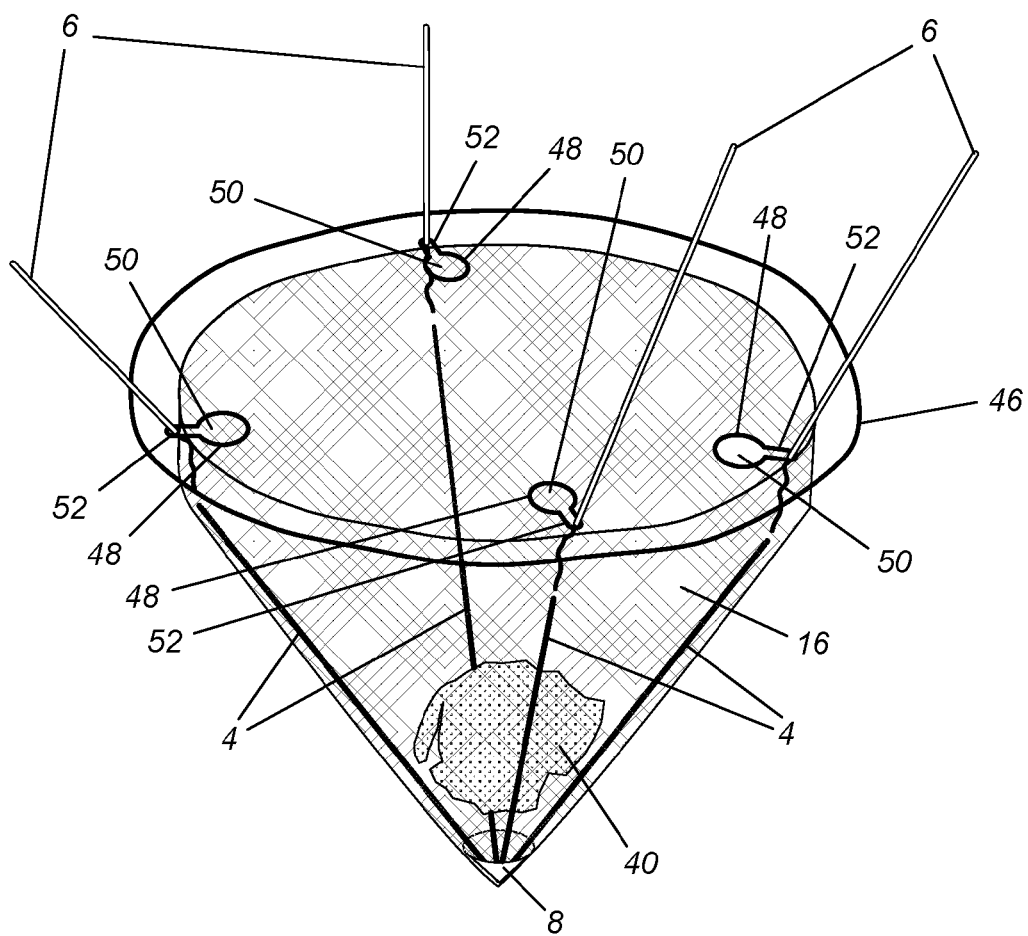
FIG. 13 is a perspective view of an open receptacle having a lid with premade holes configured to receive laparoscopic sleeves and the filaments.

FIG. 13 shows a lid 46 that covers the proximal opening 18 of the receptacle 2 and is collapsible and can expand (flattens out) when the receptacle 2 opens. The lid 46 can be identical to the membrane lid 54 with the exception that it has premade holes 48, and is interchangeable with the embodiments herein, where suitable. The lid 46 is thin and separate/removable from the receptacle 2. Preferably, the lid is sized to fit through an opening of between 14 to 20 mm when collapsed, but not when expanded in its natural open position. The lid 2 can comprise an elastic ring made of 0.6 mm nitinol, and is coered by a thin elastic material such as 1 to 3 mil gauge polyurethane film. The lid 46 includes premade holes 48, in contrast to the penetrable membrane 54. The openings 48 in FIG. 13 can be cut in any suitable shape but are preferably configured to receive at least the trocar sleeves 10, 32, 34, and 36 and preferably also the filaments 6. The number and size of the openings 48 can readily be modified depending on the number of trocar sleeves or instruments desired in the working space within the receptacle 2. This number can be 2-6, for example. Preferred openings 48 in the lid 46 are configured to receive both trocar sleeves and the filaments 6. As shown in FIG. 13 the openings 48 are shaped made in a keyhole shape, having both large 50 and smaller 52 sections. The trocar sleeves, e.g., 10, 32, 34, and 36 can pass through the larger holes 50 while the filaments 6 can pass through the smaller sections 52. The openings 48 can be keyhole shape or other shapes such as slits. Additionally, any suitable number of openings 48 can be used to match and accommodate the number of trocar sleeves and/or filaments. According to preferred embodiments, the size of the openings 48 are sized to receive their designated trocar sleeve. According to preferred embodiments the filaments 6 can be configured to align the trocar sleeves with their designated openings 48.

Furthermore, the receptacle can be designed to collapse in height alone, so that there is more room and visibility to place the specimen inside the container prior to morcellation and to better accommodate the bag inside the cavity. Once the specimen is placed in the receptacle the opening can be pulled upward (proximally) lengthening the height in preparation for the morcellation. During power morcellation each cut tissue is limited to a maximum diameter so that they can easily fit through a trocar sleeve of a slightly larger diameter. The procedure is for removal of the cut tissue through the specified sleeve during or after morcellation of the tissue, but prior to the removal of the receptacle. The distal end of the morcellator and the sleeve, from which the tissue will be removed, are within the opening of the receptacle, so that no pieces of cut tissue inadvertently fall outside the receptacle and into the abdominal cavity. Once the specimen has been cut and all the cut pieces removed, the empty bag is collapsed and removed out the same tissue removing sleeve.

Prior to its use, the receptacle can be stored inside a tube that can be used as the trocar sleeve at the time of morcellation. Alternatively, the tube, storing the receptacle, can hold the receptacle in its collapsed position as the receptacle is being inserted through a trocar sleeve previously inserted. According to preferred embodiments, there is a tubular ring around the receptacle, keeping it collapsed. This ring has a larger diameter than the inside of the trocar sleeve. Through its center is a pushrod, the pushrod can be configured to push the collapsed receptacle into the trocar sleeve and then through the tubular ring and trocar sleeve.

Insertion of the receptacle 2 into the patient's body, such as the abdominal cavity, can be accomplished any suitable way, such as by pushing the proximal ends of the collapsed support rods 4 through the hollow channel of the trocar sleeve 10 and out the distal opening 14. Preferably insertion is by pushing the distal end with base 8 though the proximal end of the sleeve 10 thereby collapsing the rods 4 and receptacle 2. Removal of the receptacle 2 through the proximal opening 22 of the trocar sleeve 10 can be done using any suitable way. As one non-limiting example, a medical practitioner can inwardly pull on filaments 6 attached to the receptacle 2 and positioned outside of the patient's body. Preferably, removal is by pulling on the drawstring 42 on the proximal end through the sleeve 10, thereby collapsing the receptacle 2, so that the receptacle can be pulled out proximal end first. According to further embodiments, the distal cap 8 of the receptacle can be attached to a distal cable 58 that a practitioner can pull on from inside the cavity to aide in the insertion of the receptacle 2. While the receptacle 2 is configured to be inserted distal end 8 first, according to certain embodiments it can be extracted either distal 8 or proximal end 18 first. For example, after closing the drawstring 42, the receptacle can be inverted and pulled up by the distal end first without spilling the contents of the receptacle 2.

Preferred methods of morcellating a targeted piece of tissue in a subject include: a) providing the morcellation receptacle described herein b) creating an incision in the subject near the targeted piece of tissue, wherein the incision has a width of between 14-20 mm and inserting a trocar sleeve into the incision; c) collapsing the receptacle; d) inserting the collapsed receptacle inside of the subject through the trocar sleeve; e) opening the proximal opening of the receptacle; f) positioning the targeted tissue into the receptacle such that cut pieces of the targeted tissue will remain within the receptacle; g) positioning a morcellator into the proximal opening of the receptacle and cutting the target tissue; h) removing the cut targeted tissue from the receptacle through the trocar sleeve; and i) collapsing the receptacle and withdrawing it from inside the subject through the trocar sleeve.

According to preferred embodiments, the targeted specimen 40 has been previously detached from its original points of attachment to the patient, so that it can be positioned into the open receptacle 2.

The preferred methods of use of the teachings herein are for laparoscopic surgery, and are directed for the morcellation receptacle 2 to be collapsed and pushed through a first trocar sleeve 10 that has a diameter of 14 to 20 mm and has been placed through the anterior wall into the patient's cavity where it self-expands open, through natural spring tension, into its natural, open position. The targeted specimen 40 that has been previously detached from its points of attachment is positioned into the open receptacle 2 through the proximal opening 18. The lid 46 can then be collapsed and pushed through the trocar sleeve 10 into the cavity, where it self-expands, and is positioned on top of the proximal opening 18 of the receptacle 2.

The proximal ends of the receptacle 2 has (3 or 4) filaments 6 attached at their distal ends. The proximal ends of the filaments 6 are grasped through the openings 48 of the lid 46, and pulled proximally through the anterior wall 12, on the outside perimeter and adjacent to the trocar sleeves 10, 32, 34, and 36 that have been previously inserted. Pulling the filaments 6 more proximal pulls the receptacle 2 with specimen 40 inside, and lid 46 on top proximally toward the inside of the anterior wall 12. The filament 6 sections positioned outside the cavity and proximal to the anterior wall are clamped with clamps 26 so that the receptacle 26 is immobilized or substantially so. The distal end 14 of the first trocar sleeve 10 is positioned through the corresponding hole 48/50 of the lid 46 and positioned so that its distal segment extends into the bag. The second, third and if necessary 4th trocar sleeves 32, 34, and, 36 are positioned through their corresponding lid openings 48/50 with their distal segments positioned inside the bag.

As shown in FIG. 15, the proximal ends of the receptacle 2 can also have three filaments 6 attached to the bag at their distal ends. At their proximal ends, the filaments 6 are grasped through the openings of the lid and pulled proximally through the anterior abdominal wall 12 on the outside perimeter and adjacent to the trocar sleeves 32, 34, and 36 that have been previously inserted. The distal end 14 of the first trocar sleeve 10 is positioned through its corresponding hole.

The electric morcellator 28 is then inserted through second trocar sleeve 32 so that the blade is inside the receptacle 2 and adjacent to the specimen 40 to be cut. For visualization, a laparoscope is inserted through any suitable trocar sleeve 36, and a first grasper 38 can be inserted through first trocar sleeve 10 and a second grasper 30 can be inserted through a fourth trocar sleeve 34 to stabilize the specimen 40 during morcellaton. The morcellated pieces are individually removed from the bag through first trocar sleeve 10, from which the receptacle 2 itself is inserted and extracted though, which preferably has a larger diameter than the other trocar sleeves. Once the receptacle 2 is empty, the morcellator 28 and graspers 30 and 38 are removed through their respective trocar sleeves 34 and 10. Additionally the laproscope is removed from its trocar sleeve 36. According to preferred embodiments, the laproscope with corresponding trocar sleeve 36 can remain inside the cavity to maintain visualization as the lid 46 and receptacle 2 are removed. The filaments 6 are released from the clamps 26. The lid 46 is collapsed and removed through the first trocar sleeve 10. The drawstring 42 on the proximal end of the bag is pulled into and through first trocar sleeve 10, collapsing the receptacle 2. The receptacle 2 is then removed through the first trocar sleeve 10.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. A morcellation receptacle system comprising:
   a collapsible receptacle, having a vertical axis with a lower half section with a distal end, and an upper half section with a proximal end, and a horizontal axis, configured such that when the collapsible receptacle is collapsed on its horizontal axis, it is linearly sized to fit within and through an opening between 14-20 mm in width but not when expanded in a natural open position; said receptacle comprising:
   (a) a distal area;
   (b) a plurality of at least three support rods positioned in a circumferential and equidistant manner around the vertical axis, or substantially so, and having proximal ends extending proximally and laterally away from the distal area and configured such that the support rods can move towards each other on the horizontal axis when the receptacle is collapsing and move away from each other on the horizontal axis when the receptacle is opening,
   (c) a flexible liner that is water resistant, low-friction, tear-resistant, and made of material different from the support rods, having a thickness between 0.05-0.15 mm, wrapped along the support rods such as to define a bag with a closed end at the distal end and a proximal opening in the upper half section of the receptacle having a width between 14-30 cm;
   (d) a plurality of at least three support filaments having distal ends coupled to the upper half section of the receptacle in a circumferential manner and configured such that when proximal ends of the support filaments are pulled away from each other, the receptacle is moved in a proximal direction and is maintained in an open position; and
   (e) a collapsible and expandable lid that covers the proximal opening in the upper half section of the receptacle when expanded, and is collapsible to fit through the 14 to 20 mm opening.

2. The morcellation receptacle system of claim 1, wherein the distal area comprises a solid distal base and has a width that is less than the proximal opening in the upper half of the receptacle, and the at least three support rods comprise distal ends that are coupled to the solid distal base.

3. The morcellation receptacle system of claim 1, wherein the distal area of the collapsible receptacle comprises sections of the support rods that are curved or bent such that at least four support rods are used wherein a first pair of support rods are made from a singular curved or bent piece and a second pair of support rods are made from another singular curved or bent piece.

4. The morcellation receptacle system of claim 3, further comprising a solid distal base that the curved or bent sections of the support rods traverse through.

5. The morcellation receptacle system of claim 1, further comprising a trocar sleeve, having a proximal and distal opening connected by a hollow channel, wherein the hollow channel has a width between 14-20 mm such that the collapsible receptacle, when collapsed on its horizontal axis, is linearly sized to fit within and through the hollow channel, but not when expanded.

6. The morcellation receptacle system of claim 1, wherein the distal ends of the plurality of at least three support filaments are coupled to the proximal ends of the at least support rods.

7. The morcellation receptacle system of claim 1, further comprising a drawstring circumnavigating around the vertical axis of the upper half section of the collapsible receptacle and configured such that when the drawstring is tightened, the support rods move towards each other on the horizontal axis to collapse the proximal opening of the receptacle, and conversely when the drawstring is loosened, the support rods move away from each other on the horizontal axis to open the proximal opening of the receptacle.

8. The morcellation receptacle system of claim 7, wherein the drawstring is in direct contact with the support rods, such that the tightening of the drawstring directly collapses the support rods towards each other on the horizontal axis.

9. The morcellation receptacle system of claim 7, wherein the drawstring is not in direct contact with the support rods, such that the tightening of the drawstring directly collapses the flexible liner which in turn collapses the coupled support rods towards each other on the horizontal axis.

10. The morcellation receptacle system of claim 1, wherein the lid has one or more openings configured to allow a trocar sleeve to traverse through.

11. The morcellation receptacle system of claim 1, wherein the distal area of the collapsible receptacle comprises a pointed spike that extends proximally and is within the flexible liner.

12. The morcellation receptacle system of claim 1, wherein the lid is a membrane without premade holes and is configured to be penetrated by trocar sleeves.

13. A method of morcellating a targeted piece of tissue in a subject comprising:
  a) providing the morcellation receptacle system of claim 1;
  b) creating one or more incisions in the subject near the targeted piece of tissue, wherein the incision has a width of between 14-20 mm and inserting a first trocar sleeve into a first incision;
  c) collapsing the receptacle;
  d) inserting the collapsed receptacle inside of the subject through the first trocar sleeve;
  e) opening the proximal opening of the receptacle;
  f) positioning the targeted piece of tissue into the receptacle such that cut pieces of the targeted piece of tissue will remain within the receptacle;
  g) positioning a morcellator into the proximal opening of the receptacle and cutting the target piece of tissue;
  h) removing the cut targeted piece of tissue from the receptacle through the first trocar sleeve; and
  i) collapsing the receptacle and withdrawing it from inside the subject through the first trocar sleeve.

14. The method of morcellating of claim 13, wherein the distal area of the collapsible receptacle comprises sections of the support rods that are curved or bent such that at least four support rods are used wherein a first pair of support rods are made from a singular curved or bent piece and a second pair of support rods are made from another singular curved or bent piece.

15. The method of morcellating of claim 14, further comprising a solid distal base that the curved or bent sections of the support rods traverse through.

16. The method of morcellating of claim 13, wherein the first trocar sleeve has a proximal and distal opening connected by a hollow channel with a width between 14-20 mm such that the collapsible receptacle, when collapsed on its horizontal axis, is inserted and removed within and through the hollow channel of the first trocar sleeve and wherein the cut targeted piece of tissue is removed from the receptacle through the hollow channel of the first trocar sleeve.

17. The method of morcellating of claim 16, further comprising providing a second trocar sleeve having a proximal and distal end connected by a hollow channel, and inserting the second trocar sleeve into the subject through one of the incisions such that the distal end of the second trocar sleeve is positioned within the opened receptacle and the morcellator is inserted and removed within and through the hollow channel of the second trocar sleeve, and travels proximally and distally within the hollow channel of the second trocar sleeve during cutting.

18. The method of morcellating of claim 13, further comprising a drawstring circumnavigating around the vertical axis of the upper half section of the collapsible receptacle and configured such that when the drawstring is tightened, the support rods move towards each other on the horizontal axis to collapse the proximal opening of the receptacle, and conversely when the drawstring is loosened, the support rods move away from each other on the horizontal axis to open the proximal opening of the receptacle.

19. The method of morcellating of claim 18, wherein the drawstring is in direct contact with the support rods, such that the tightening of the drawstring directly collapses the support rods towards each other on the horizontal axis.

20. The method of morcellating of claim 18, wherein the drawstring is not in direct contact with the support rods, such that the tightening of the drawstring directly collapses the flexible liner which in turn collapses the coupled support rods towards each other on the horizontal axis.

21. The method of morcellating of claim 13, wherein the lid has one or more openings configured to allow a trocar sleeve to traverse through.

22. The method of morcellating of claim 13, wherein the lid is a membrane without premade holes and is configured to be penetrated by trocar sleeves.

\* \* \* \* \*